(12) United States Patent
Hirano

(10) Patent No.: US 7,504,240 B2
(45) Date of Patent: Mar. 17, 2009

(54) METHODS FOR SYNTHESIZING POLYNUCLEOTIDES USING A SINGLE PRIMER

(75) Inventor: Masanori Hirano, Cascata Nishisugamo 503, 6-8-6, Takinogawa, Kita-ku, Tokyo 114-0023 (JP)

(73) Assignee: Masanori Hirano, Tokyo (JP)

( * ) Notice: Subject to any disclaimer, the term of this patent is extended or adjusted under 35 U.S.C. 154(b) by 0 days.

(21) Appl. No.: 11/078,841

(22) Filed: Mar. 10, 2005

(65) Prior Publication Data

US 2006/0204973 A1 Sep. 14, 2006

(51) Int. Cl.
C12P 19/34 (2006.01)
C12Q 1/68 (2006.01)

(52) U.S. Cl. .................................. 435/91.2; 435/91.1

(58) Field of Classification Search ........................ None
See application file for complete search history.

(56) References Cited

U.S. PATENT DOCUMENTS

| | | | | | |
|---|---|---|---|---|---|
| 5,242,795 | A | * | 9/1993 | Croco | 435/6 |
| 5,470,722 | A | * | 11/1995 | Jones | 435/91.2 |
| 5,789,206 | A | * | 8/1998 | Tavtigian et al. | 435/91.2 |
| 5,962,272 | A | * | 10/1999 | Chenchik et al. | 435/91.1 |
| 6,114,149 | A | * | 9/2000 | Fry et al. | 435/91.2 |
| 6,232,067 | B1 | * | 5/2001 | Hunkapiller et al. | 435/6 |

FOREIGN PATENT DOCUMENTS

| | | | |
|---|---|---|---|
| DE | 4438630 A1 | * | 5/1996 |
| JP | 2004-073118 | | 3/2004 |
| WO | WO 9109944 A2 | * | 7/1991 |
| WO | WO 2004013354 A1 | * | 2/2004 |

OTHER PUBLICATIONS

Suzuki et al. ("Construction and characterization of a full length-enriched and a 5'-end-enriched cDNA library" Gene. Oct. 24, 1997;200(1-2):149-56).*
Russell ("Improved single-strand conformation polymorphism analysis by asymmetric polymerase chain reaction with end-labeled primers" Genet Anal Tech Appl 1994;11(1):24-7).*
Suzuki et al. ("Construction and characterization of a full length-enriched and a 5'-end-enriched cDNA library" Gene. Oct. 24, 1997;200(1-2):149-56).*
Suzuki et al. ("Construction and characterization of a full length-enriched and a 5'-end-enriched cDNA library" Gene. Oct. 24, 1997;200(1-2):149-56).*
Chenchik et al., "Full-length cDNA cloning and determination of mRNA 5' and 3' ends by amplification of adaptor-ligated cDNA," BioTechniques, 21:526-534 (1996).
Cheng et al., "Effective amplification of long targets from cloned inserts and human genomic DNA," Proc Natl Acad Sci USA, 91:5695-5699 (1994).
Diatchenko et al., "Suppression subtractive hybridization: a method for generating differentially regulated or tissue-specific cDNA probes and libraries," Proc Natl Acad Sci USA, 93:6025-6030 (1996).
Frohman et al., "Rapid production of full-length cDNAs from rare transcripts: amplification using a single gene-specific oligonucleotide primer," Proc Natl Acad Sci USA, 85:8998-9002 (1988).
Hirano, "RACE using only a gene-specific primer," Mol Biotechnol, 27:179-186 (2004).
Hirano and Noda, "Genomic organization of the mouse Msh4 gene producing bicistronic, chimeric and antisense mRNA," Gene, 342:165-177 (2004).
Jobling and Gill, "Encoded evidence: DNA in forensic analysis," Nat Rev Genet, 5:739-751 (2004).
Matz et al., "Amplification of cDNA ends based on template-switching effect and step-out PCR," Nucleic Acids Res, 27:1558-1560 (1999).
Shames et al., "Identification of widespread Helicobacter hepaticus infection in feces in commercial mouse colonies by culture and PCR assay," J Clin Microbiol, 33:2968-2972 (1995).
Stanford et al., "Gene-trap mutagenesis: past, present and beyond," Nat Rev Genet, 2:756-768 (2001).
"Marathon™ cDNA Amplification Kit User Manual," Clontech Laboratories, Inc., Protocol # PT1115-1 (PR15735), pp. 1-55 (2001).
"SMART™ RACE cDNA Amplification Kit," Clontechniques, January, pp. 4-6 (1999).
"GeneRacer™ RLM-RACE Kit," Invitrogen Life Technologies, catalog (2002).
Bertling et al., "Determination of 5' ends of specific mRNAs by DNA ligase-dependent amplification," PCR Methods Appl., 3(2):95-9 (1993).
Frohman et al., "Rapid amplification of complementary DNA ends for generation of full-length complementary DNAs: thermal RACE," Methods in Enzmology,218:340-56 (1993).
Troutt et al., "Ligation-anchored PCR: a simple amplification technique with single-sided specificity," Proc. Natl. Acad. Sci. USA, 89:9823-9825 (1992).

* cited by examiner

Primary Examiner—Kenneth R. Horlick
Assistant Examiner—Christopher M. Babic
(74) Attorney, Agent, or Firm—Medlen & Carroll, LLP

(57) ABSTRACT

An objective of the present invention is to provide methods for synthesizing polynucleotides comprising an unknown nucleotide sequence in a region containing their 5'-end. By using a single gene-specific primer, nucleotide sequences complementary to each other are added respectively at the 5'-and 3'-ends of a desired polynucleotide, to synthesize a desired polynucleotide. Requisite nucleotide sequences can be easily added by incubating with a primer, double-stranded DNA, and template-dependent DNA polymerase. By applying the present invention to 5' RACE, genes expressed in a low-level, which cannot be obtained by known methods, have been efficiently obtained.

14 Claims, 6 Drawing Sheets

MSH30 ---GAGGCCAGGGTCCTCCGCATGGGGCATC₃·switch (SEQ ID NO:16)
      ---CTGACTACGAAGCTGGTCTCAAATGACT₅----#21 (SEQ ID NO:17)

MSH32 ---TATAGCATAAGATCTTTGTTTCCAAAT₃·switch (SEQ ID NO:18)
      ---CGTAGGGTAAGAACTTTTTATAGACGT₅----#20 (SEQ ID NO:19)

MSH51 ---CCTCACTTGGCACTCTTACTTACTGGCC₃·switch (SEQ ID NO:20)
      ---GAGACGGAGGACTCACGACCCTAATTTC₅----#27 (SEQ ID NO:21)

MSH53 ---TCATTAGCAGTTGCTCACATGTCTTGGA₃·switch (SEQ ID NO:22)
      ---GTCTGATCACCAGTAGAATCCGAACGAG₅----#31 (SEQ ID NO:23)

MSH74 ---TCAAGTTGACACAAAACTAGCCAATACA₃·switch (SEQ ID NO:24)
      ---CGAAGCTGGTCTCAAATGACTGTGAAAT₅·#21 (SEQ ID NO:25)

MSH75 ---TCAAGTTGACACAAAACTAGCCAATACA₃·switch (SEQ ID NO:24)
      ---CGAAGCTGGTCTCAAATGACTGTGAAAT₅·#21 (SEQ ID NO:25)

FIG.4

METHODS FOR SYNTHESIZING POLYNUCLEOTIDES USING A SINGLE PRIMER

FIELD OF THE INVENTION

The present invention relates to methods for amplifying polynucleotides using a single primer. More particularly, the present method relates to a simple method for accurate polynucleotide amplification using only a single, gene-specific primer, without an anchor or adaptor primer.

BACKGROUND OF THE INVENTION

Isolation of full-length complementary deoxyribonucleic acid (cDNA) is a key step in the investigation of gene expression, gene function, protein structure, and protein-protein interactions. The polynucleotide amplification process is one of the most important steps of the isolation process. The most common technique for amplifying polynucleotides is the PCR (polymerase chain reaction) method. DNA syntheses by the PCR method involve repetitive complementary chain syntheses in the direction from a primer to the 3' end. In the PCR method, newly synthesized DNA is utilized as a template after denaturation, and thus the reaction products exponentially increase. Primers used in the PCR reaction comprise nucleotide sequences complementary to the 3'-side region of a desired nucleotide sequence. Accordingly, the nucleotide sequence of at least a region to be annealed by a primer should be known in advance. In other words, DNA of unknown nucleotide sequence cannot be selectively amplified by the PCR method.

However, circumstances exist wherein DNAs of unknown nucleotide sequence need to be selectively amplified. For example, it is often necessary to elicit a full-length gene based only on its partial nucleotide sequence. However, it is particularly difficult to synthesize a cDNA from the 5'-side region of an mRNA. Accordingly, cDNAs having incomplete 5'-side nucleotide sequences are often cloned. To reveal the full-length nucleotide sequence of an incomplete cDNA lacking a 5'-side nucleotide sequence requires the selective amplification of DNAs comprising such unknown 5'-end nucleotide sequences.

In addition, differential display methods, whose goal is to acquire genes having specific functions, often results in the acquisition of nucleotide fragments and partial gene sequences. When the resulting nucleotide sequences do not match with known gene sequences, identification of the entire nucleotide sequence of these genes is required. In such cases, acquisition of full-length genes based on fragmentary nucleotide sequences is attempted.

Methods for acquiring the full-length gene based on a partial gene sequence are known. A typical method is the RACE (rapid amplification of cDNA ends) method. With this method, the region between a known site and each end of an unknown mRNA sequence is amplified (Frohman, M. A. et al., Proc. Natl. Acad. Sci. USA 1988 December, 85: 8998-9002). Specifically, the RACE method employs a gene having unknown terminal nucleotide sequence as a template, and amplifies a region containing that unknown nucleotide sequence by PCR using primers directed to a region of known nucleotide sequence. By determining the nucleotide sequence of the PCR products, the unknown nucleotide sequence can be revealed. There are some known variations of the RACE method, including, for example, the SMART (switching mechanism at 5' end of RNA transcript) method (Nucleic Acids Res. 27/6, 1558-1560, 1999) and the Marathon-ready cDNA method, both supplied by Clontech. Other variations of the RACE method are also known. For example, by ligating both ends to cyclize the DNA, and by using a region of known nucleotide sequence, a PCR primer can be designed even for a DNA having unknown nucleotide sequences at its ends. However, this method lacks specificity for the 5'-end of mRNA. Accordingly, it is particularly unsuitable for acquisition of a full-length gene having unknown 5'-side. Another method involves the linking of an oligonucleotide of known sequence to the 3'-end of a cDNA first strand. However, this method requires a step of purifying the first strand after synthesis.

While the currently known methods have their advantages and have proved to be quite useful, problems still arise. For example, because nonspecific products are often amplified, the specific target cDNA makes up only a small fraction of the total yield. Thus, acquiring the full-length sequence of a gene having low transcription level remains difficult, particularly in circumstances where the mRNA is longer. Accordingly, a new RACE method capable of acquiring full-length sequences based on a very small amount of mRNA would be of particular benefit.

SUMMARY OF THE INVENTION

An objective of the present invention is to provide a new principle for synthesizing a polynucleotide having an unknown nucleotide sequence in a region containing its 5'-end. Herein, a simple and accurate improved RACE method that makes use of only a single, gene-specific primer, without the requirement of anchor or adaptor primers, is provided.

Such a single-primer-based PCR method was previously believed to be impossible. While not wishing to be bound by existing theory, the present method involves the exact synthesis of cDNA ends under conditions such that amplified products obtain a characteristic structure, namely a terminal inverted repeat composed of a gene-specific primer and occasionally several nucleotides from its 3'-flanking sequence. These structures suggest a hypothetical mechanism of cDNA synthesis in which polymerases synthesize a sequence complementary to the gene-specific primer at the 3' end of the daughter strand by switching the template to the 5' terminal region through circularization of the DNA. As a result, the targeted DNA is efficiently amplified with only a single, gene-specific primer. This technique, which provides highly specific amplification of the 5' and 3' ends of a cDNA is especially useful for isolation of cDNA when the corresponding mRNA is scarce.

In the RACE method, a desired gene is synthesized by utilizing a primer-dependent complementary chain synthesis reaction, such as PCR. Generally, in primer-dependent complementary chain synthesis reactions, the nucleotide sequence of the primer is designed based on the nucleotide sequence of the polynucleotide to be synthesized. On the other hand, an objective of the RACE method is to synthesize a region whose nucleotide sequence is unknown. Thus, which nucleotide sequence to select as the primer annealing nucleotide sequence and how to introduce that nucleotide sequence are major obstacles that determine the performance of the RACE method. For example, when using the current RACE method, little is known about which nucleotide sequences are suitable to be introduced to give desirable results. There also remains room for improvement in the introduction methods for nucleotide sequences.

Accordingly, in view of these circumstances, the present inventors discovered that the performance of the RACE method is improved when specific nucleotide sequences are added to the 3'-end of the complementary chain, which is synthesized upon complementary chain synthesis for template polynucleotides comprising unknown nucleotide sequence at their 5'-side. The present inventor further discovered preferable reaction conditions for this objective and, thus, completed the present invention.

Specifically, the present invention relates to the following methods:

[1] A method for synthesizing a polynucleotide having an unknown nucleotide sequence in a region comprising its 5'-end, wherein the method comprises the steps of:
   a) synthesizing a complementary strand of the polynucleotide using an oligonucleotide that anneals with a region of the polynucleotide as a primer;
   b) adding a nucleotide sequence complementary to the oligonucleotide of step a) to the 3'-end of the complementary strand synthesized in step a); and
   c) synthesizing the polynucleotide having the unknown nucleotide sequence in the 5'-end region using the complementary strand obtained in step b) as a template and the oligonucleotide in step a) as the sole primer.

[2] The method of [1], wherein step b) comprises incubating the following (1) to (3) under conditions where a complementary strand synthesis reaction is feasible,
   (1) an enzyme catalyzing a template-dependent complementary strand synthesis reaction,
   (2) the polynucleotide synthesized in step a), and
   (3) nucleotide substrates.

[3] The method of [1], wherein the polynucleotide having the unknown nucleotide sequence in the 5'-end region is a cDNA second strand.

[4] The method of [3], wherein the cDNA is synthesized using an mRNA in which a polynucleotide comprising a nucleotide sequence that is substantially the same as that of the oligonucleotide of step a) is added to the 5'-end as a template.

[5] The method of [3], comprising the step of synthesizing the polynucleotide having the unknown nucleotide sequence in the 5'-end region by incubating the following (i) to (iii) under conditions where a complementary strand synthesis reaction is feasible:
   (i) a cDNA first strand;
   (ii) an enzyme catalyzing a template-dependent complementary strand synthesis reaction; and
   (iii) nucleotide substrates.

[6] The method of [5], wherein an enzyme having reverse transcriptase activity is used as the enzyme of (ii) that catalyzes the template-dependent complementary strand synthesis reaction.

[7] The method of [1], wherein the polynucleotide having the unknown nucleotide sequence in the 5'-end region is a cDNA first strand.

[8] The method of [7], wherein the polynucleotide is a cDNA synthesized using an oligo-dT primer having an arbitrary nucleotide sequence added to its 5'-end.

[9] A method for isolating a polynucleotide whose terminal nucleotide sequence is unknown, wherein the method comprises the step of cloning a polynucleotide synthesized by the method of [3] or [7].

[10] A method for screening mRNA samples, ds cDNA libraries, and genomic DNA libraries for a polynucleotide of interest comprising the steps of:
   a) synthesizing a complementary strand of the polynucleotide of interest by using an oligonucleotide that anneals with a region of the polynucleotide as a primer;
   b) adding a nucleotide sequence complementary to the oligonucleotide of step a) to the 3'-end of the complementary strand synthesized in step a); and
   c) synthesizing the polynucleotide of interest using the complementary strand obtained in step b) as a template and the oligonucleotide in step a) as the sole primer; and
   d) screening for the presence of said polynucleotide.

[11] A method for identifying insertion sites of DNA elements at the nucleotide sequence level in the chromosomes of a mutant or transformed cell comprising the steps of:
   a) extracting genomic DNA from a mutant or transformed cell;
   b) digesting the genomic DNA;
   c) amplifying the genomic ends of the extracted DNA using a single primer sequence specific to a marker gene;
   d) screening for the presence of the marker gene; and
   e) identifying the insertion site or mutant gene into which a DNA element has been inserted.

[12] A method for identifying a site of gene translocation at the nucleotide sequence level comprising the steps of:
   a) synthesizing a complementary strand of fusion of genomic DNA known to be result from gene translocation by using an oligonucleotide that anneals with a region of the polynucleotide as a primer;
   b) adding a nucleotide sequence complementary to the oligonucleotide of step a) to the 3'-end of the complementary strand synthesized in step a); and
   c) synthesizing the polynucleotide of interest using the complementary strand obtained in step b) as a template and the oligonucleotide in step a) as the sole primer; and
   d) screening for the presence of chimeric mRNA that corresponds to the genomic fusion DNA.

This novel PCR method, using only a single primer, is applicable to not only RACE but also amplification of genomic DNA (RAGE). However, while the method of the present invention (i.e., a single primer PCR method) is an extraordinarily powerful tool when used with in PCR screening, for the purpose of isolating a region containing an unknown sequence, in particular, it not be suitable for quantitative or qualitative (semi-quantitative) analyses (e.g., RT-PCR for expression analysis).

These and other objects and features of the invention will become more fully apparent when the following detailed description is read in conjunction with the accompanying figures and examples. However, it is to be understood that both the foregoing summary of the invention and the following detailed description are of a preferred embodiment, and not restrictive of the invention or other alternate embodiments of the invention.

BRIEF DESCRIPTION OF THE DRAWINGS

FIG. 4 depicts the possible basepair interaction in the daughter strand. Possible basepair interactions (black letters without underlines) between the 3' terminal sequences and 3' flanking sequences of a gene-specific primer in the daughter strand are shown. The numbers represent the sequences of the gene-specific primer. The dotted black lines represent sequences that together with gene-specific primers form inverted repeats (FIGS. 2A and 2B).Daughter strand sequences are shown as follows: MSH30 3' terminal (SEQ ID NO:16) and MSH30 5' flanking (SEQ ID NO:17): MSH32 3' terminal (SEQ ID NO:18) and MSH32 5' flanking (SEQ ID NO:19); MSH51 3' terminal (SEQ ID NO:20) and MSH51 5' flanking (SEQ ID NO:21); MSH53 3' terminal (SEQ ID NO:22) and MSH53 5' flanking (SEQ ID NO:23); MSH74 3' terminal (SEQ ID NO:24)and MSH74 5' flanking (SEQ ID NO:25); and MSH75 3' terminal (SEQ ID NO:24) and MSH75 5' flanking (SEQ ID NO:25).

DETAILED DESCRIPTION OF THE INVENTION

The words "a", "an", and "the" as used herein mean "at least one" unless otherwise specifically indicated.

Figure 1:
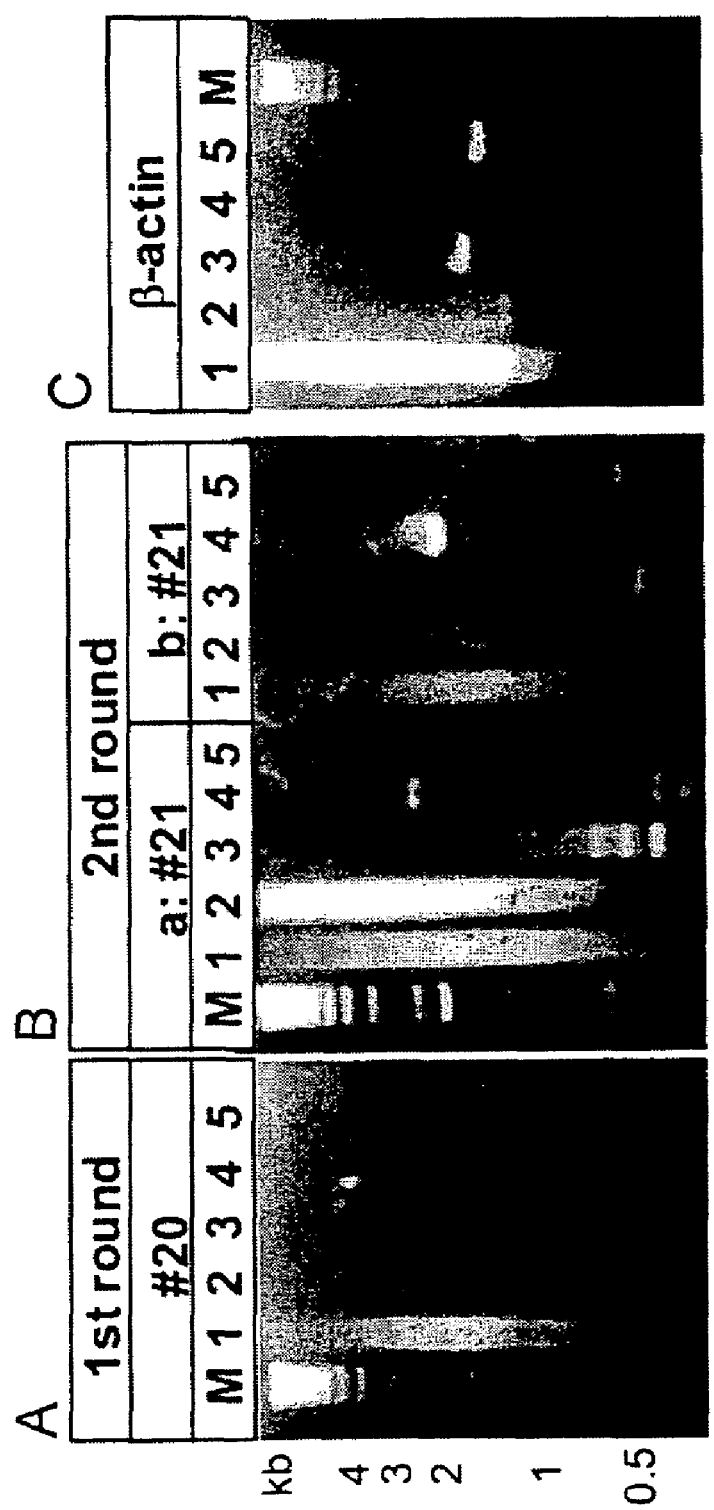
FIG. 1 shows the results of agarose gel electrophoresis of RACE PCR products obtained using the standard protocol described in Example 1. A, First-round 5' RACE PCR using #20 and adaptor primers. B, Second-round 5' RACE PCR using nested #21 and adaptor primers; note that 5 µl of the first-round sample (a, b) were used for the second-round RACE PCR. C, 3' RACE PCR of β-actin. 3' RACE PCR was carried out with β-actin-specific and adaptor primers. In all three panels, the adaptor primer was used at concentrations of 10 µM (lane 1), 1 µM (lane 2), 0.1 µM (lane 3) and 0.01 µM (lane 4); results obtained in the absence of adaptor primer are shown in lane 5.

PCR is a method for amplifying a target DNA, in which primers are typically placed at arbitrary positions in the 5'- and 3'-sides of the target gene's DNA (or cDNA for RT-PCR), and the reaction consisting of denaturation, annealing, and extension (synthesis) steps are repeated by a thermal cycler to amplify the region between the two primers with thermostable Taq DNA polymerase (Saiki R K et al., Science 1988 Jan. 29, 239(4839): 487-491). In the RACE methods, (1) single-stranded cDNAs are synthesized from mRNA template by using a reverse transcriptase and gene-specific primers, and then an anchor DNA is linked to the 3'-end of the synthesized ss cDNA (5'-RACE) (oligo-dT and gene-specific primers are used in 3'-RACE) or (2) an adaptor DNA is ligated to both ends of double-stranded cDNA by using DNA ligase. Thus, unknown sequences can be amplified by PCR using a gene-specific primer and a primer complementary to the nucleotide sequence of the anchor or adaptor DNA (Frohman et al., supra; Chenchik A. et al., Biotechniques, 1996 September, 21(3): 526-34). Herein, the inventor demonstrates that target cDNA ends can be amplified more efficiently and specifically by the RACE using gene-specific primers only and without using any adaptor primers (FIG. 1). Furthermore, this method has led to successful isolation of mouse Msh4 gene's variant cDNAs, which have interesting structures and functions, and whose expression levels were quite low (Hirano M. and Noda, T., Gene, 2004 Nov. 10, 342(1): 165-77; Hirano M., Mol. Biotechnol., 2004, 27: 179-187). These reports suggest that the establishment of a new methodology for DNA (or cDNA) amplification by PCR technology that employs a single primer only, in addition to the conventional PCR techniques employing two kinds of primers.

Single Primer Method

Accordingly, the present invention provides a single primer method for synthesizing polynucleotides that comprise a region of unknown nucleotide sequence containing the 5'-end, the methods comprising the steps of:

a) synthesizing a complementary strand of the polynucleotide by using an oligonucleotide that anneals with a region of the polynucleotide as a primer;

b) adding a nucleotide sequence complementary to the oligonucleotide of step a) to the 3'-end of the complementary strand synthesized in step a); and c) synthesizing the polynucleotide having the 5'-end region of unknown sequence using the complementary strand obtained in step b) as a template and by using the oligonucleotide in step a) as a primer.

Figure 2:
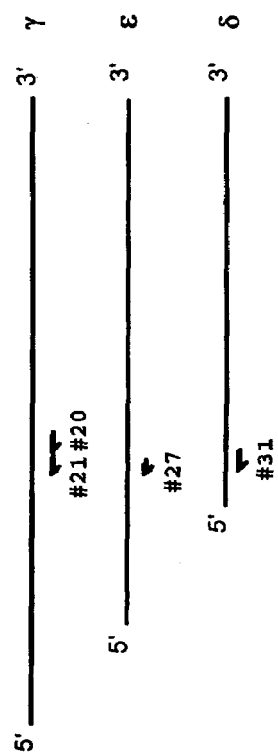
FIGS. 2A and 2B depict the sequences of the 5' and 3' termini of the 5' RACE products. Sequences of both ends of the 5' RACE products are shown as follows: MSH30 5' (SEQ ID NO:7) and MSH30 3' (SEQ ID NO:8); MSH32 5' (SEQ ID NO:9) and MSH52 3' (SEQ ID NO:8); MSH51 5' (SEQ ID NO:10) and MSH51 3' (SEQ ID NO:11); MSH53 5' (SEQ ID NO:12) and MSH53 3' (SEQ ID NO:13); MSH74 5' (SEQ ID NO:14) and MSH74 3' (SEQ ID NO:15) and MSH75 5' (SEQ ID NO:14) and MSH75 3' (SEQ ID NO:15).Plasmid names are shown at the left. Bold black letters without underlines show the gene-specific primer sequences, whose names are shown at the right. Boxed letters show sequences that together with the gene-specific primer form inverted repeats. MSH30 and MSH32 contain Msh4 variant α cDNA; MSH51 contains Msh4 variant ε cDNA; MSH53 contains Msh4 variant δ cDNA; and MSH74 and MSH75 contain Msh4 variant θ and τ cDNA, respectively (Hirano and Noda, Gene, 2004, 342: 165-177).
FIG. 2C is a schematic representation of the position of the gene-specific primers.
Figure 3A:
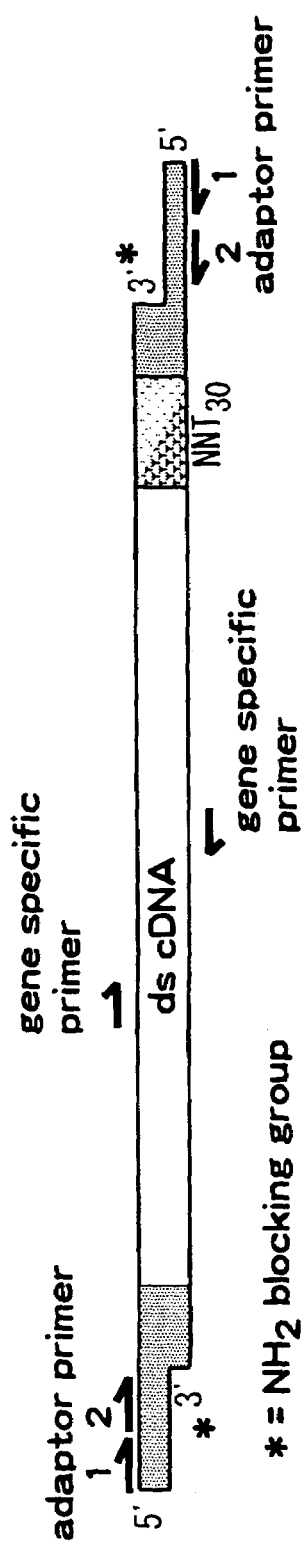
FIG. 3A depicts the reaction principle of the Marathon cDNA amplification kit used in the Examples. In the figure, "1" indicates the position to which an adaptor primer anneals, and "2" indicates the position to which an adaptor primer for nested PCR anneals. "ds cDNA" means double-stranded cDNA, and "NNT30" indicates a primer used in the cDNA synthesis.
Figure 3B:
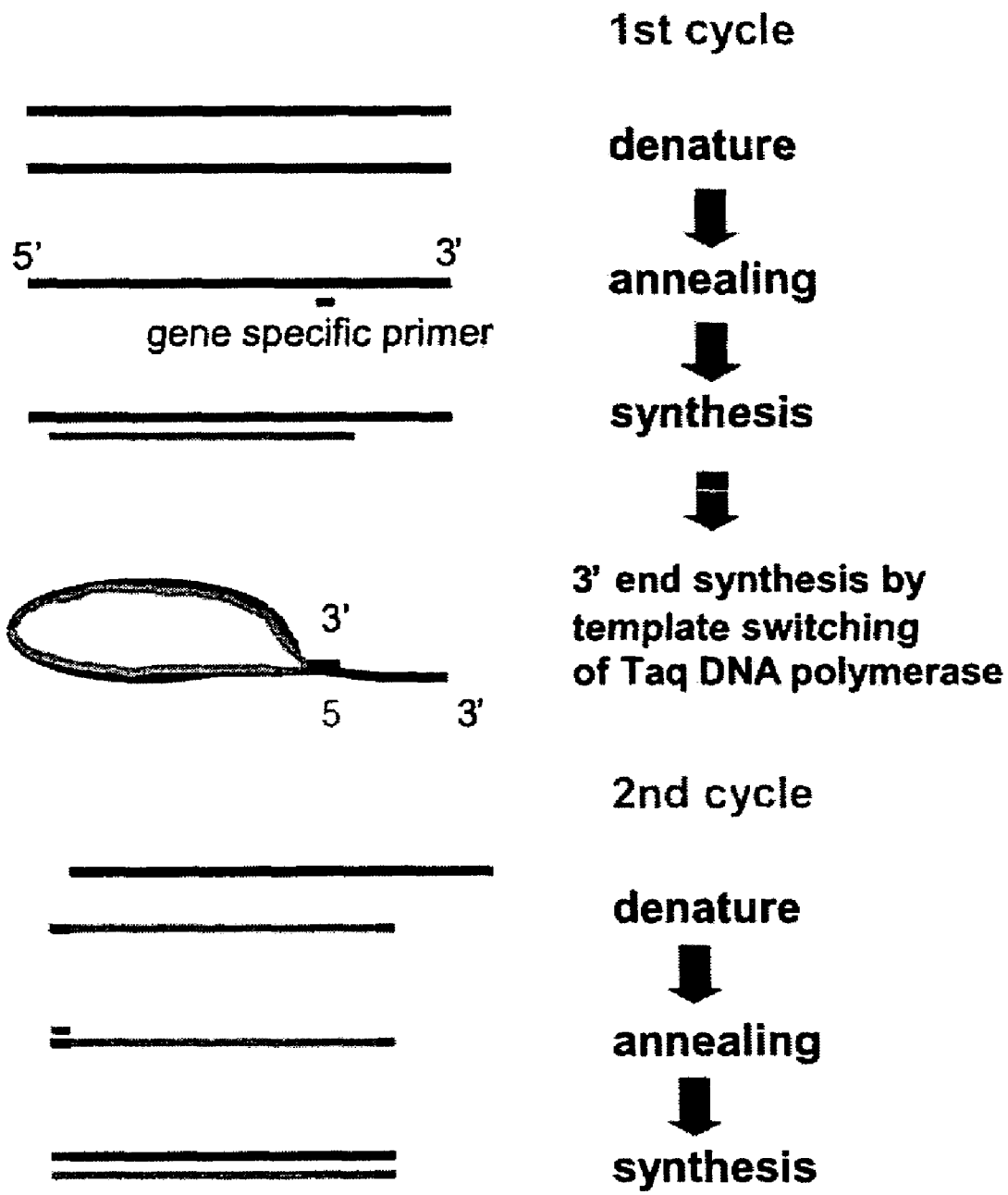
FIG. 3B depicts a hypothetical mechanism of RACE using only a single gene-specific primer. Hypothetical process of cDNA end synthesis is shown. Details are discussed herein.
Figure 5:
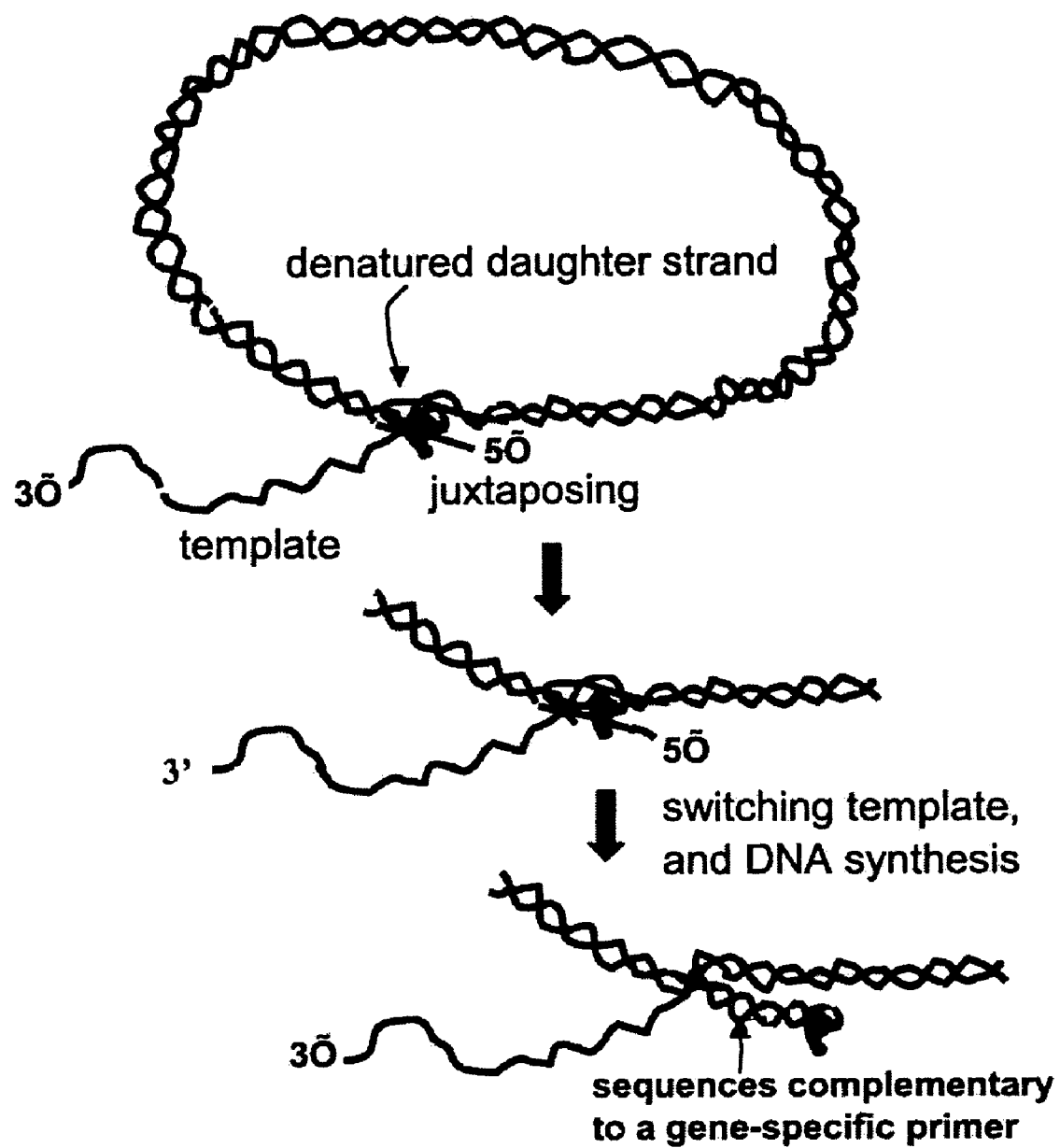
FIG. 5 is a model for the formation of the circular DNA through template-switching of Taq DNA polymerase.

A hypothetical mechanism for the single-primer-based synthesis of cDNA end is illustrated in FIG. 3B. Similarly, a model for the formation of the circular DNA through template-switching of Taq DNA polymerase is illustrated in FIG. 5. In the PCR using Taq DNA polymerase, DNA elongation (synthesis) reaction is carried out at high temperatures (68-72° C.). Furthermore, linear DNA tends to form a circular structure at lower concentrations (Heffron, F. et al., Proc. Natl. Acad. Sci. USA, 1978 December, 75(12): 6012-6). Thus, Taq DNA polymerase, which has finished the DNA synthesis to the 5'-end of the template, approaches to a daughter strand, which has been denatured from the naked terminal region of dsDNA synthesized from a gene-specific primer at the temperature of 68° C., as is observed at the cohesive end of the λ phage. Under such circumstances, a single-stranded DNA portion (the 5'-end of the daughter strand) of a circular molecule get into the catalytic domain of Taq DNA polymerase (by passive diffusion mechanism), and then be juxtaposed to the double-stranded DNA that has been synthesized. As the next step, Taq DNA polymerase switches the template to the single-stranded DNA (template-switching), and further continues the DNA synthesis. The template-switching event is thought to occur at various positions. However, the length of the terminal inverted repeat falls within the range of 24-34 bp in every obtained cDNA clone (data not shown; see FIG. 2). Possible reasons for this phenomenon are as follows. Of those DNAs synthesized through template-switching mechanism, DNAs having 40-50 bp or longer terminal inverted repeats may not be amplified due to the suppression PCR effect (Diatchenko L. et al., Proc. Natl. Acad. Sci. USA, 1996 June, 93(12): 6025-30). Alternatively, a region that dissociates from dsDNA by denaturation may be limited within the first 40 bp or less at the DNA end at 68° C. (this length of denaturation may also depend on the GC content). In addition, only cDNAs having the nucleotide sequence perfectly complementary to the gene-specific primer (24 bases) are then selectively amplified in the subsequent cycles of PCR. These factors are thought to cause predominant amplification of cDNAs having terminal inverted repeat of 24-34 bp (amplification of the fittest). Complementary DNAs, which have terminal inverted repeat structures comprising a gene-specific primer with or without several nucleotides adjacent to its 3' end, are made (or amplified) by the proposed mechanism described above.

In the present invention, polynucleotides having unknown 5'-end nucleotide sequences in a region containing the 5'-end include every polynucleotide capable of serving as a template for complementary chain synthesis. Specifically, DNA, RNA, hybrid polynucleotides thereof, and polynucleotides comprising various nucleotide derivatives are included. Polynucleotides include not only naturally occurring polynucleotides but also artificially produced polynucleotides. Alternatively, polynucleotides in which artificial mutations are introduced into naturally occurring polynucleotides can also be used.

The particularly important polynucleotides in the present invention are mRNA and/or cDNA. As used herein, cDNA includes both the first and the second strands. mRNA and regions containing 5'-end of cDNA synthesized using mRNA as a template are important polynucleotides whose nucleotide sequences often need to be determined.

In the present invention, the phrase "unknown nucleotide sequence in a region containing the 5'-end" means that the nucleotide sequence of regions containing the 5'-end is unknown in the polynucleotides that serve as a template for complementary chain synthesis in the above-described step a). Accordingly, if those polynucleotides are produced using another polynucleotide X as a template, the 3'-side nucleotide sequence of the polynucleotide X is unknown.

When the polynucleotide X is an mRNA, its 3'-end is typically poly (A). In the present invention, the phrase "mRNA whose nucleotide sequence in a region containing the 3'-end is unknown" means that the nucleotide sequences in the 3'-end region, with the exception of the poly (A) tail at the 3'-end, are unknown. For cDNA synthesized using a region of mRNA containing its 3'-end as a template, it is said that the 5'-end nucleotide sequence of the polynucleotide is unknown if a nucleotide sequence of regions containing the 5'-end, with the exception of the "t" stretch, is unknown, regardless of the presence or absence of the "t" stretch arranged at its 5'-end.

However, the 3'-end to which a predetermined nucleotide sequence is added in step b) can be the 3'-end of a complementary strand produced from the "t" stretch as a template. That is, poly (A) is not considered in deciding whether a nucleotide sequence is known or unknown. On the other hand, on adding a nucleotide sequence to the 3'-end, and if an "a" stretch is present at the 3'-end, the nucleotide sequence can be added to the 3'-end of an "a" stretch.

In the present invention, the above-described step a) of synthesizing complementary strands of polynucleotides using an oligonucleotide that anneals with a region of polynucleotides can be carried out using any enzymes that catalyze primer-dependent complementary chain synthesis reaction. Examples of such enzymes include, but are not limited to, Taq polymerase.

Oligonucleotides used as a primer in step a) are not limited with respect to their nucleotide sequences and lengths, so long as they can anneal with a region of the above-described polynucleotides, prime complementary chain synthesis, and thereby enable synthesis of complementary strands to the 5'-end of the polynucleotides. To initiate complementary chain synthesis reaction keeping a certain level of specificity, oligonucleotides comprising at least about 15 nucleotides or more, usually about 20 to 40 nucleotides, for example about 20 to 30 nucleotides, are generally used as primers. Methods for preparing such oligonucleotides are well known in the art.

Nucleotide sequences constituting oligonucleotides comprise nucleotide sequences complementary to any region of the above-described polynucleotides. In the context of the present invention, the term "complementary", as in "complementary nucleotide sequence", refers to nucleotide sequences capable of forming base pairs (complementary strand annealing) according to the Watson-Crick rule. Nucleotide sequences of the oligonucleotides of the present invention need not be completely complementary. That is, oligonucleotides capable of initiating complementary chain synthesis under stringencies where specificity can be maintained are included in the oligonucleotides of the present invention, even if the corresponding nucleotide sequences are not completely complementary. For example, the complementarity of nucleotides located at the 3'-end of the primers to the templates is an important condition. However, it is not always necessary that middle portions or the 5'-end of the primers be completely complementary to the templates.

In the present invention, the nucleotide sequence of the above-described polynucleotides in a region containing 5'-end is unknown. However, there may be some parts of known nucleotide sequences, apart from that noted region. Accordingly, oligonucleotides of the present invention can be designed so as to comprise a nucleotide sequence complementary to such parts of known nucleotide sequences. When the above-described polynucleotides are cDNA, oligonucleotides are designed so as to anneal with a region of known nucleotide sequence in the nucleotide sequence constituting that gene, and to prime complementary strand synthesis in the direction towards the region of unknown nucleotide sequence.

Following the step a), the present invention comprises a step b) of adding nucleotide sequences complementary to the oligonucleotides of step a) to the 3'-end of the complementary strands synthesized in step a). This step b) can be carried out by any conventional method. Examples of step b) in the present invention include the following methods. That is, step b) can be carried out by incubating the following (1) to (3) under conditions where a complementary strand synthesis reaction is feasible:

(1) an enzyme catalyzing a template-dependent complementary strand synthesis reaction;
(2) the polynucleotide synthesized in step a); and
(3) nucleotide substrates.

Examples of such enzymes include Taq DNA polymerase (Boehringer Mannheim), ExTaq DNA polymerase and TAKARA Taq (Takara Shuzo Co., Ltd.), AmpliTaq (Applied Biosystems), Tfl and Tth (Promega), etc.

In the above step, nucleotide substrates, which can be used as substrates by enzymes catalyzing a template-dependent complementary chain synthesis reaction, are added. Specifically, nucleotide substrates generally used in the PCR method or cDNA syntheses can be used. Typically, naturally occurring deoxynucleotides of "a", "t", "c" or "g" are used. In addition, nucleotide derivatives having modifications, such as fluorescent molecules, radioisotopes, or biotins, can be used as necessary.

These elements together with the polynucleotides of (2) that have been synthesized in step a) are incubated under the conditions where complementary strand synthesis reactions are feasible, thereby enabling the addition of nucleotide sequences which are complementary to that of the above-described oligonucleotides to the 3'-end of the polynucleotide synthesized in step a). To date, this reaction, of incubating the above-described elements to add desired nucleotide sequences to the 3'-end of DNA, has not been reported by others. The present inventor discovered that desired nucleotide sequences can be added to the end of polynucleotides under the above-described specific conditions, and that thus-added nucleotide sequences enable the synthesis of polynucleotides having unknown terminal end nucleotide sequences, and thus completed the present invention.

Addition of nucleotide sequences to the 3'-end of the above polynucleotides, by incubating the elements (1) to (3), can be explained by the following mechanism (FIG. 3B). Polynucleotides of (2) that have been synthesized in step a) form duplex with template polynucleotides. Linear double-stranded DNA become circular particularly at low concentrations, and both ends come close to each other (Heffron et al., In vitro mutagenesis of circular DNA molecule by using synthetic restriction site. Proc. Natl. Acad. Sci. USA. 75:6012-6016, 1978). Though not wishing to be bound by theory, it is believed that DNA in solutions are physically stabilized by taking a circular form.

Such duplexes are stabilized when DNA is placed at a temperature sufficient for stabilization. However, under conditions where complementary strand synthesis reactions are carried out, using thermostable DNA polymerases or such, DNA is placed under considerably high temperature conditions. For example, a high temperature of about 70° C. is required for the complementary chain synthesis reactions by Ex-Taq (Takara Shuzo Co., Ltd.). Under such high temperature conditions, the duplex structure of the ds DNA terminal regions cannot be stably maintained. As a result, the 3'-ends of the DNAs approach strands other than the strand with which the 3'-ends should form base-pairs, and may initiate complementary chain synthesis with this strand as a template. In the present invention, this phenomenon is called "template switching" of DNA polymerases.

Strand switching occurs most easily between ends of linear DNA whose ends have come close to each other by taking a circular structure. Specifically, the 3'-end approaches the 5'-end of the same strand, and causes synthesis of a strand complementary to that 5'-end nucleotide sequence. As a result, a nucleotide sequence complementary to the 5'-end of the strand is added to the 3'-end of the same strand. Since the 5'-end of the strand is the nucleotide sequence of the above-described primer oligonucleotide, addition to the 3'-end of a sequence complementary to the above-described oligonucleotide results.

In the present invention, mechanisms of adding desired nucleotide sequences to the 3'-end of polynucleotides is not limited to the above-described mechanism. With any mechanisms, the step b) is accomplished by incubation under the conditions described herein. This is also supported by the results described in the Examples.

When the polynucleotide of the present invention comprises a cDNA, the cDNA may be either a first strand or a second strand. First strands of cDNA are DNA synthesized using mRNA as a template. Second strands refer to DNA synthesized using the cDNA first strand as a template. When second strands are used as a template, DNA synthesis progresses in a direction toward 5' of mRNA, and thus 5' RACE can be carried out. On the other hand, when first strands are used as a template, DNA synthesis progresses in a direction toward 3' side of mRNA, and thus 3' RACE can be carried out. To use second strands as a template, primers having nucleotide sequences complementary to the second strand are designed. When a first strand is a template, the nucleotide sequence of a primer shall be a nucleotide sequence complementary to the first strand. The 5'-side of a second strand of cDNA (i.e., the 5'-side of mRNA) comprises a translation initiation codon. Accordingly, the region at the 5'-side of a second strand is important for deducing a translated amino acid sequence based on the nucleotide sequence of cDNA. Therefore, determination of nucleotide sequences of this region often emerges as important challenges in gene isolation and functional analysis.

When second strands of cDNA are used as the polynucleotides in the present invention, the second strands can be synthesized by incubating the following (i) to (iii) under conditions where complementary chain synthesis is feasible:
(i) a first strand of cDNA,
(ii) an enzyme catalyzing a template-dependent complementary strand synthesis reaction, and
(iii) nucleotide substrates.

In the present invention, first strands of cDNA described in (i) can be synthesized with an enzyme having reverse transcriptase activity and using, as a primer, an oligonucleotide having a nucleotide sequence complementary to any region of mRNA. Primers for the first strand synthesis are preferably oligonucleotides having the same nucleotide sequence as the oligonucleotide used in the step a) described above. In general cDNA synthesis methods, mRNA used as a template is decomposed after the first strand synthesis. mRNA can be easily decomposed by alkaline denaturation or by the action of enzymes, such as RNase H. When mRNA is decomposed, the first strand of cDNA becomes a single strand. In the present invention, the enzyme catalyzing a template-dependent complementary chain synthesis reaction used in synthesis of the second strand or in step b) can also be used as the reverse transcriptase for synthesis of the first strand. DNA polymerases also having reverse transcriptase activity, such as Tfl or Tth, are known in the art. These DNA polymerases are commercially available (Promega). By using such enzymes, the number of enzymes in the reaction system can be reduced.

The second strand of cDNA is a DNA synthesized with thus obtained first strands as a template. As the template-dependent complementary strand synthesis reaction, complementary chain synthesis reaction starting from the 3'-end of the primer is usually utilized. Nucleotide sequence-specific annealing of primers enables the specific synthesis of nucleotide sequences. However, the primer is not an essential factor for complementary strand synthesis. For example, when the above elements (i) to (iii) are incubated under conditions where the complementary strand synthesis is feasible, the complementary strand synthesis reaction is accomplished using the first strand of cDNA as a template. As used herein, the conditions where the complementary strand synthesis is feasible refer to conditions where the above element (ii), namely, an enzyme catalyzing template-dependent complementary strand synthesis reaction, can maintain its activity. Such conditions vary with the enzyme used. However, those skilled in the art can suitably determine conditions necessary for maintaining enzymatic activity, depending on the enzyme used.

Examples of the step b), of adding a nucleotide sequence complementary to the oligonucleotide of step a) to the 3'-end of the complementary strand synthesized in step a) in the present invention, include the following methods. For example, mRNA in which a polynucleotide comprising substantially the same nucleotide sequence as the above oligonucleotide of step a) has been added at its 5'-end may be used as a template to synthesize the cDNA first stand. In the 3'-end of a thus synthesized first strand, a nucleotide sequence complementary to the nucleotide sequence of the above oligonucleotide is arranged. That is, this cDNA first strand is the very polynucleotide desired in step b).

Methods for linking arbitrary oligonucleotides to the 5'-end of mRNA are known. For example, the oligo-capping method, which is a method of synthesizing a full-length cDNA, is a method for specifically linking an oligonucleotide called an oligo-cap linker to the 5'-end of mRNA (Murayama, K. and Sugano, S. (1994) Oligo-capping: a simple method to replace the cap structure of eukaryotic mRNAs with oligoribonucleotides. Gene 138, 171-174). The oligo-capping method connects a linker to a target capping structure present at the 5'-end of eukaryotic mRNA. Accordingly, contamination with cDNA derived from incomplete mRNA that lacks a capping structure at the 5'-end can be prevented.

To apply the oligo-capping method to the present invention, oligo-cap linkers having substantially the same nucleotide sequence to that of the above-described oligonucleotide are used. In a general oligo-capping method, it is advantageous to use oligo-cap linkers with nucleotide sequences hardly found in the gene so that full-length cDNA is specifically amplified. This is because that a possibility of amplification of gene fragments rather than the full-length cDNA cannot be ruled out when a nucleotide sequence found in the gene is used. In the present invention, on the other hand, a nucleotide sequence complementary to the above oligonucleotide is introduced in the 3'-end. Thus the nucleotide sequence of the linker is a nucleotide sequence found in the gene. In the present invention, oligonucleotides can be added to the 5'-end of mRNA by the same procedure as in the oligo-capping method except that the nucleotide sequence of the linker is different.

By using a cDNA library of the present invention, cDNA can be isolated based on the nucleotide sequences of unknown genes identified by a genome project. Once cDNA is cloned, protein analyses can be carried out based on the cDNA. The cDNA library of the present invention can also be utilized in isolation of known gene's splicing variants having low expression level. If cDNA libraries derived from various tissues are synthesized according to the present invention, it would have vital use to isolate genes and splicing variants.

In the present invention, step c) can be carried out for example by the PCR method. Specifically, the polynucleotide obtained in step b) is denatured into a single strand. In the PCR method, the template polynucleotide is denatured generally by heating. The denatured polynucleotide together with a primer oligonucleotide is incubated under conditions where a complementary chain synthesis starting from this primer is feasible. Depending on the nucleotide sequence of the primer and the composition of a reaction solution, those skilled in the art can select conditions that allow complementary chain synthesis to occur. By repeating denaturation and complementary chain synthesis reaction, a desired polynucleotide can be continuously produced by the PCR method.

As a DNA polymerase catalyzing complementary strand synthesis, use of thermostable enzymes (i.e., enzymes which are not inactivated even at the polynucleotides' denaturation temperature) is advantageous. If a DNA polymerase used as an enzyme catalyzing the template-dependent complementary chain synthesis reaction in (1) or (ii) has thermostability, it can be directly used in step c).

Polynucleotide synthesized in step c) can be separated by known methods, including but not limited to, ethanol precipitation. Alternatively, techniques such as electrophoresis can be used to separate polynucleotides of desired size.

The method for synthesizing polynucleotides according to the present invention is useful for cloning polynucleotides having unknown nucleotide sequences in a region containing their 5'-end. In other words, the present invention relates to methods for isolating polynucleotides having unknown nucleotide sequences at their ends, that is methods comprising a step of cloning polynucleotides having unknown nucleotide sequences in the 5'-end region that have been synthesized according to the method of the present invention.

Methods for cloning synthesized polynucleotides are conventional in the art. Generally, synthesized polynucleotides can be cloned by integrating them in suitable cloning vectors for TA cloning.

The determination of the nucleotide sequence of polynucleotides thus cloned is possible. A nucleotide sequence of an inserted polynucleotide is determined by utilizing primers having a nucleotide sequence complementary to the nucleotide sequence of a vector, etc. By these steps described above, the 5' RACE is available when nucleotide sequences of a region containing second strand's 5'-end is unknown, and the 3' RACE is available when nucleotide sequences of a region containing first strand's 5'-end is unknown.

The application of the methods for synthesizing a polynucleotide according to the present invention is not limited to RACE. For example, telomerase activities can be measured according to the method of the present invention. Telomerases utilize DNA comprising specific nucleotide sequences as a substrate, and add nucleotide sequences comprising a repetition of a specific nucleotide sequence called "telomere repeats" to the 3'-end of the substrate DNA. Telomere repeats are composed of a nucleotide sequence specific for each species. For example, human telomere repeat is (TTAGGG)n. Based on the length of the added telomere repeat, telomerase activities can be evaluated.

Because the complementary chain thus synthesized has a nucleotide sequence complementary to the substrate DNA, an oligonucleotide comprising the same nucleotide sequence as the substrate DNA can be used as a primer to synthesize a complementary chain (step a). The substrate DNA remaining in the reaction solution can also be directly used as a primer. When complementary chain synthesis reaches the 5'-end, cyclization of double strand DNA and template switching action occurs, and a nucleotide sequence complementary to the substrate DNA is added to the 3'-end (step b). Finally, oligonucleotides having the same nucleotide sequence as the substrate DNA can be used to amplify an unknown nucleotide sequence at the 3'-end of the substrate DNA that has been extended by the telomerase activity.

It is evident that the nucleotide sequence added by the action of telomerase is a telomere repeat. However, the length of the telomere repeat and how many nucleotides in the repeat unit is contained in the terminal telomere repeat are unknown. Accordingly, DNAs synthesized using, as a template, substrate DNA elongated by telomerase activity is included as a polynucleotide having an unknown nucleotide sequence in a region containing its 5'-end in the present invention.

Elements necessary for the method for synthesizing polynucleotides according to the present invention can be combined to provide kits for synthesis of polynucleotides containing an unknown nucleotide sequence. Kits according to the present invention can be composed of, for example, the following elements:

buffer solution capable of maintaining the DNA polymerase activity; and nucleotide substrates for complementary chain synthesis
The specific constitution of each element in the present invention is as described above. In addition to the elements described above, additional elements can be added to the kits of the present invention. For example, reverse transcriptases for synthesizing cDNA first strands or oligo dT primers for carrying out 3' RACE can be combined. Oligonucleotide primers designed for a region of known nucleotide sequences in the desired polynucleotides can also be pre-attached.

When linkers are to be introduced into 5'-end of mRNAs, oligonucleotides to be used as linkers and an RNA ligase can be combined. Furthermore, when the oligo-capping method is applied to bind linkers to mRNA's 5'-end, various enzymes necessary for the oligo-capping method are combined. For example, alkaline phosphatase (BAP) and tobacco acid pyrophosphatase (TAP) can be combined.

To examine the adequacy of the experimental materials and procedures, controls can be combined with the kits of the present invention. Examples of such controls suitable for use in the context of the present invention include, but are not limited to, primers expected to synthesize cDNA of a certain size regardless of the kinds of cDNA library used. Primers giving such cDNA include a primer capable of synthesizing a β-actin gene.

Applications

1. RACE

When a Taq DNA polymerase (Tfl or Tth) having reverse transcriptase activity is used in the cDNA first strand synthesis, the single primer method is applicable to the conventional RACE in which every reaction cycle is initiated from mRNA template, though it may be necessary to prolong the reverse transcription reaction (i.e., denaturation and extension in the first cycle). Exemplary prolonged reaction conditions include, but are not limited to, denaturation at 94° C. for five minutes; annealing at 60° C. for one minute; and extension at 72° C. for 10-20 minutes. When template switching occurs in this cycle under such conditions, the amplification runs smoothly. Then, PCR can be carried out under the typical conditions, though, again, it is preferably to prolong the extension steps. Since the temperature for extension is approximately 70° C., formation of mRNA higher-order structures are inhibited, and, as a result, the frequency of premature termination of cDNA synthesis is reduced even in GC-rich regions. In addition, full-length cDNA may more readily be isolated even when the template mRNA is exceedingly larger in size.

As noted above, the present invention provides kits for the synthesis of polynucleotides containing an unknown nucleotide sequence. An exemplary RACE kit of the present invention may include the following: (i) PCR buffer; (ii) polymerase, such as Tfl or Tth, for example; (iii) control gene-specific primer; and (iv) protocol (e.g., the first thermal cycles of: denaturation at 94° C. for five minutes; annealing at 60° C. for one minute; and extension at 72° C. for 10-20 minutes). An mRNA isolation kit may optionally be included.

2. Screening of a cDNA Library

Instead of screening a cDNA library constructed with λ phage vector using a $^{32}$P-labeled DNA probe, a ds cDNA (library) may be screened using single primer RACE of the present invention Genomic library screening is also contemplated and as discussed in detail below, in section 4. An exemplary ds cDNA (i.e., library) synthesis and screening kit may include the following: (i) ds cDNA synthesis kit and (ii) a PCR kit, including, for example, buffer, polymerase, and protocol.

3. Rescue of a DNA Element Inserted into Chromosome

The single primer method of the present invention may be used to identify insertion sites of DNA elements in the chromosome of a mutant cells (human, mouse, rat, etc.) or mutant organisms (mouse, *Drosophila*, Nematoda, Zebra fish, *Arabidopsis*, maize, yeast, *E. coli*, etc.) created by insertional mutagenesis using retrovirus, transposon, and plasmid DNA (e.g., the gene trap method using the neo gene or such) at the nucleotide sequence level. See Stanford W. L. et al., Nature Review Genetics, 2001 October, 2(10): 756-68.

An exemplary application is as follows: Genomic DNA is extracted from mutant cells or tissue, and then digested with an appropriate restriction enzyme or fragmented by shearing. Then RAGE (for rapid amplification of genomic DNA ends, see section 4 below)-PCR is carried out according to the single primer method using the extracted DNA and a primer specific to a marker gene (e.g., lacZ, neo, and EGFP) present in the DNA element used for insertional mutagenesis. The nucleotide sequence of the amplified DNA is determined so as to identify the site (i.e., gene) into which the DNA element is inserted. The use of the method described above is expected to permit the simple, rapid, accurate rescue rather than (1) the *E. coli* transformation-based rescue method, (2) the inverse PCR-based rescue method, or such. In other words, a high throughput system covering the series of processes from mutagenesis to mapping may be established.

When a DNA polymerase having reverse transcriptase activity, such as Taq polymerase (i.e., Tfl or Tth), is used, the single primer method can be used to isolate cDNA derived from chimera mRNA produced through gene trap events.

An exemplary insertional mutagenesis kit of the present invention may include the following: (i) a genomic DNA purification kit for cells or tissues; (ii) a PCR kit for rescuing vector and flanking genomic DNA (e.g., PCR primers for both directions and protocol), and (iii) an optional RACE kit. Vectors specific to the host organism(s) may also be required.

4. Amplification of Genomic DNA (RAGE)

The single primer method of the present invention may also be applied to the LA-PCR, in which large size genomic DNA fragments are amplified. Specifically, the single primer method is applicable to RAGE (rapid amplification of genomic DNA ends)-PCR, RAGE-based screening of genomic library, RAGE-based chromosome walking (rolling) to fill gaps in sequences assembled by WGS (whole-genome shotgun sequencing), and the like. An exemplary RAGE PCR kit of the present invention may include the following: (i) LA-PCR; (ii) Taq DNA polymerase; and (iii) control PCR primer 5. Diagnostic Uses The single primer method of the present invention may also be used to identify sites for chromosome (gene) translocation at the nucleotide sequence level. For example, when one focuses on a gene that is known to cause leukemia upon chromosome translocation, one may use the techniques of the present invention to examine for the presence or absence of translocations in a gene by (1) searching for a chimeric mRNA from patient's leukemia cells, and (2) determining site of fusion in genomic DNA.

When using mRNA as the primary template, the single primer method of the present invention may be applicable, for example, to the detection of viral RNA, and the like. Detection accuracy and sensitivity may be improved by using the single primer method, as compared with the conventional PCR using two types of primers, because the single primer method reduces mis-annealing and non-specific DNA amplification caused thereby.

6. Forensic Applications

The single primer method of the present invention may improve detection accuracy and/or sensitivity for a desired portion of genomic DNA in a trace amount of sample DNA. The present invention is applicable to the amplification of longer fragments of genomic DNA, as discussed in section 4 above. Accordingly, the present invention is applicable in the field of forensic science and medicine. See Jobling, M. A. and Gill, P., Nature Review Genetics, 2004 October, 5(19):739-51. Specifically, the single primer method facilitates the setting of primers at various positions in a target gene. The method also allows doubling the number of target DNAs to be separated at the same cost.

The success of the forensic and diagnostic utilities depends largely on the frequency of the template-switching event to occur. It is therefore beneficial to optimize the conditions that facilitate template switching (i.e., conditions for the extension such as temperature, reaction time, etc.).

Simulation experiments are also available to test the method of the present invention. For example, it is possible to test the effectiveness of the present method by (1) introducing a trace amount of viral DNA (cDNA) or bacterial DNA (cDNA) into a human genomic DNA (cDNA) sample, and (2) carrying out detection experiments. Limiting dilution experiments are also useful in such evaluation. Alternatively, detection sensitivity and/or accuracy, as well as the number of cycles required for the detection, and others can be compared between the ordinary double (two) primer method and the single (one) primer method.

Hereinafter, the present invention is described in more detail by reference to the Examples. However, the following examples only illustrate aspects of the invention and in no way are intended to limit the scope of the present invention

EXAMPLES

Example 1

General Methods

1. Polymerase Chain Reaction Primers:

The gene-specific primers used in the examples of the present invention are as follows:

```
#20:
5'-GGTATTGTTGGCGACAGGTTTCTC-3';      (SEQ ID NO: 1)

#21:
5'-GGGATGCCATCCTTGTTTGATTGC-3';      (SEQ ID NO: 2)

#27:
5'-AAGAGACTGTCAGGCATGGTAGTG-3';      (SEQ ID NO: 3)

#31:
5'-GATGACTTCTGGATGGGGCCATGG-3';      (SEQ ID NO: 4)
and

β-actin:
5'-GTGACGAGGCCCAGAGCAAGAG-3';        (SEQ ID NO: 5)
for 3'RACE
```

The adaptor primer sequence is as follows:

```
5'-CCATCCTAATACGACTCACTATAGGGC-3'    (SEQ ID NO: 6)
```

2. mRNA Preparation

Poly(A) RNA was prepared from the testis of 8-week-old C57BL/6J mice using FastTrack mRNA Isolation kits (Invitrogen) as instructed by the manufacturer.

3. Template cDNA Synthesis

First strand cDNA was synthesized in 10 µl of reaction mixture containing 2 µl of 5× reaction buffer (250 mM Tris (pH 8.5), 40 mM $MgCl_2$, 150 mM KCl and 5 mM dithiothreitol (DTT)), 1 µl deoxynucleotides-triphosphate mix (dNTP mix; 10 mM), 1 µl of 10 µM oligo(dT) primer, 1 µg of poly(A) RNA, 2 µl of sterile water and two units of avian myeloblastosis virus (AMV) reverse transcriptase at 42° C. for one hour. Second strand cDNA was synthesized in 100 µl of reaction mixture containing 20 µl of 5× reaction buffer (100 mM of Tris, pH 7.5, 500 mM KCl, 50 mM ammonium sulfate, 25 mM $MgCl_2$, 0.75 mM β-nicotine adenine dinucleotide (NAD) and 0.25 mg/ml bovine serum albumin (BSA)), 10 µl of first strand mixture, 2 µl of 10 mM dNTP mix, 63 µl of sterile water and 5 µl of a cocktail containing *E. Coli* DNA polymerase I (6 units/µl), RNase H (0.25 units/µl) and *E. coli* DNA ligase (1.2 units/µl) at 16° C. for two hours. Half of the second strand mixture (50 µl) was then treated with 10 units of T4 DNA polymerase at 16° C. for one hour, after which it was extracted with phenol and precipitated with ethanol. The precipitate was dissolved in 5 µl of sterile water and ligated to adaptor DNA in a 10 µl reaction mixture containing 2 µl of 5×ligation buffer (250 mM Tris-HCl, pH 7.8, 50 mM $MgCl_2$, 5 mM DTT, 5 mM ATP and 25% polyethylene glycol), 5 µl of double-stranded cDNA, 2 µl of adaptor DNA, and four units of T4 DNA ligase at 16° C. overnight. After inactivation of the ligase, the adaptor-ligated and unligated cDNAs were diluted to about 0.5 ng/µl with Tris-ethylenediaminetetraacetic acid (EDTA) buffer (TE buffer), pH 7.5.

4. Standard Conditions of RACE PCR

PCR was carried out in a reaction mixture containing 5 µl of 10×PCR buffer (250 mM TAPS buffer (pH 9.3 at 25° C.), 500 mM KCl, 20 mM $MgCl_2$ and 10 mM 2-mercaptoethanol), 2.5 µl of 2.5 mM 4dNTPs, 2 µl of testis cDNA (about 1 ng), 0.5 µl (2.5 units) of Ex-Taq (Takara), 1 µl of gene-specific primer (10 µM), 1 µl of adaptor primer (10 µM) and 38 µl of distilled water. The amplification protocol entailed 25 cycles of denaturation at 94° C. for 30 seconds, annealing at 60-62° C. for one minute, and extension at 68° C. for three minutes. One-fifth of product was subjected to 1% agarose gel electrophoresis.

5. RACE PCR with Reduced Amounts of or without Adaptor Primer

To reduce the amount of adaptor primer used, the original adaptor primer (10 µM) was diluted 2-, 3-, 4-, 5-, 10-, 100- and 1000-fold with TE buffer (pH 7.5) and 1 µl of each dilution was used for RACE PCR. When no adaptor primer was used, 1 µl of TE (pH 7.5) was added to the reaction mixture. The PCR conditions were essentially the same as the standard one described above, except for the concentration of adaptor primer. If the amount of product obtained with 25 cycles of PCR was inadequate, a second round of PCR was carried out using 5 µl of the first round sample under the same PCR conditions.

6. DNA Cloning and Sequencing

Amplified DNA fragments were separated by 1% agarose gel electrophoresis, purified using a Geneclean II kit (BIO101), and cloned into pCR2.1 using TA Cloning Kits (Invitrogen). The DNA sequences were determined using an ABI PRISM Dye Terminators Cycle Sequencing kit (Applied Biosystems); after cycle sequencing, DNA samples were resolved by gel electrophoresis on an ABI PRISM 373A DNA Sequencer (Applied Biosystems).

Example 2

RACE PCR Carried Out under Standard and Modified Conditions

Mouse Msh4 was selected as a gene to be amplified. Msh4 is a member of MutS mismatch repair gene family and has been identified in *S. cerevisiae, C. elegans*, mice and humans (Ross-Macdonald and Roeder, Cell 79:1069-80 (1994); Zalevsky et al., Genetics 153:1271-83 (1999); Kneitz et al., Genes Dev. 14:1085-97 (2000); Paquis-Flucklinger et al., Genomics 44:188-94 (1997)). While the nucleotide sequence of Msh4 is known, experiments were carried out to acquire its splicing variant.

To obtain the full-length cDNA for mouse Msh4, nested primers #20 and #21 from Example 1 for 5' RACE were designed from the sequence within the short coding region of the Msh4 variant γ cDNA, which was isolated by screening a mouse testis cDNA library using the approximately 200-bp product of degenerate PCR as a probe (data not shown). As a control, a β-actin-specific primer for 3' RACE was designed. Thereafter, with the standard PCR protocol described in Example 1, RACE PCR was carried out using gene-specific and adaptor primers on double-stranded testis cDNA to which an adaptor was ligated at both ends (Chenchik A et al., Biotechniques, 1996, supra.). An aliquot of the reaction solution was subjected to agarose-gel electrophoresis. By staining with ethidium bromide, DNA in the agarose gel was detected.

As shown in FIG. 3A, an adapter primer is designed to have the same sequence as the adaptor's single strand overhang at 5'-end. Since the 3'-end of the oligonucleotide constituting the adaptor is blocked with an $NH_2$ group, complementary chain synthesis starting from this 3'-end is suppressed. Accordingly, complementary chain synthesis from the adaptor primers does not occur in principle without complementary chain synthesis from the gene specific primer. However, under the above conditions, nonspecific products were synthesized to give smear background and the target cDNA was barely detectable (FIGS. 1A, B and C; lane 1). It was thought that this smear background was produced by nonspecific reactions, which occurred due to the adapter primer's nucleotide sequences or other factors. The manual for the Marathon cDNA amplification kit supplied by Clontech points out the possibilities of these nonspecific reactions. For example, it is described therein that a complementary chain is synthesized for the overhang region of the adaptor linked to cDNA, and cDNA can be amplified without complementary chain synthesis from the gene specific primer.

In some cases, modification of the PCR protocol—e.g., increasing the annealing temperature, using the hot-start method (D'Aquila, R. T. et al., Nucleic Acids Res., 1991, 19: 3749; Chou, Q. et al., Nucleic Acids Res., 1992, 20:1717-23) or using touchdown PCR (Don, R. H. et al., Nucleic Acids Res., 1991, 19: 4008; Hecker, K. H. and Roux, K. H., Biotechniques., 1996 20: 478-85)—improved RACE performance, enabling DNA bands to be detected on agarose gels, at the lower extent of the background smear. Unfortunately, determination of approximately 25 cDNA fragments (0.5-1.1 kb) amplified independently using the aforementioned modified conditions showed that all were nonspecific products that contained no sequence homologous to Msh4.

Example 3

Optimization of RACE PCR by Reducing the Adaptor Primer

The smear products, which were the main problem when RACE was carried out using adaptor-ligated double-stranded cDNA as a template, were thought to be caused by end-to-end amplification of various cDNAs from the adaptor primer. To suppress synthesis of nonspecific smear products, RACE PCR was initially carried out using 2- to 5-fold less adaptor primer than used in the standard protocol, but found that the results were essentially the same as with the standard level of adaptor primer; even with a 10-fold reduction in adaptor primer, nonspecifically amplified smear products were still observed (FIGS. 1B and C; lane 2). On the other hand, 100- and 1000-fold reductions in adaptor primer clearly improved the specificity of RACE PCR, as the nonspecific smear products were nearly eliminated, and the putative target cDNAs were observed as a single large band after two rounds of PCR for Msh4 or one round for β-actin (FIG. 1B-*a*, -b; lane 4 and 1C; lane 3). Moreover, the sequences of these products (approx 1.9, 1.7 and 1.6 kb) were consistent with the targeted genes, Msh4 and β-actin. Unexpectedly, none of these cDNAs contained adaptor primer sequences; instead they contained the sequences of the gene-specific primer at their 5' and 3' (β-actin) ends. In MSH30, the 5' end contained the sequence of gene-specific primer #21 and seven nucleotides from its 3' flanking sequence, which together formed a terminal inverted repeat (FIG. 2A). In MSH32, the cDNA contained the structure sandwiched between nested gene specific primers used for the first (#20 in 5' end) and second (#21 in 3' end) rounds of PCR (FIG. 2A). It thus appeared that only the gene-specific primer was necessary to accomplish cDNA ends amplification.

Example 4

RACE PCR Using Only Gene-Specific Primer(s) without an Adaptor Primer

To confirm this intriguing finding, RACE was carried out using double-stranded cDNA without a ligating adaptor—i.e., using only a gene-specific primer and the standard RACE PCR protocol (FIGS. 1A, B and C; lane 5). The amplified product was an approximately 1.5 kb DNA fragment (FIG. 1C; lane 5), which sequence analysis revealed to be β-actin cDNA. Moreover, when additional RACE experiments were carried out using only a single gene-specific primer (#21, #27 and #31; FIG. 1C and Example 1), a number of variant Msh4 cDNAs were obtained. Subsequent sequence analyses showed that all of the amplified cDNAs contained terminal inverted repeats including nucleotide sequence derived from the gene-specific primer and occasionally several nucleotides from its 3'-flanking sequence (FIG. 2B). In addition, several bases were deleted from the 5'-terminal primer sequence in one clone (MSH32; FIG. 2A), though nucleotide insertions at the 5' end were rarely observed. In FIG. 2, bold black letters show the gene-specific primer sequences, and boxed letters show sequences that together with the gene-specific primer form inverted repeats. The fact that there are sequences complementary to regions other than the primer (boxed letters) supports that complementary sequences (i.e., inverted repeats) were synthesized by template switching. Comparison of each amplified cDNA with the genomic DNA sequences confirmed that no other changes in the DNA sequence—e.g., rearrangements and internal deletions or insertions—had occurred. The cycling time required to obtain enough product (all Msh4 variants required two rounds of 25 cycles, while β-actin required only one round) is assumed to have depended on the amount of targeted mRNA present in the preparation from the target tissue.

Using this single primer RACE method, the Msh4 α, β, δ, ε, θ and τ variants were successfully identified, in addition to the Msh4 γ, which has previously been identified (Hirano and Noda, Gene, 2004, 342:165-177).

By this experiment, amplification of cDNA of the following size was confirmed for each Msh4 splicing variant. The present invention has proven that a region comprising an unknown nucleotide sequence can be amplified over sufficient length by using a single primer. In the experiment, only primers for variants γ and ε was used. The variants synthesized by this experiment comprised the same exon as that of variant γ or ε. Accordingly, various kinds of variants were synthesized by using the primers for variants γ and ε. For example, each of variants α, β, θ and τ comprised a nucleotide sequence to which primers #20 and #21 anneals.

α: about 2 kb

β: about 2 kb and about 1.5 kb

δ: about 1 kb

ε: about 2 kb

θ: about 1.5 kb

τ: about 1.5 kb

As is evident from gel photographs in FIG. 1, cDNA is amplified as a very clear band by the method of the present invention, as long as the PCR conditions are optimal and a target is present. The present invention's methods for synthesizing polynucleotides are a very unique and highly reliable method. The fact that no abnormalities were observed in the terminal nucleotide sequences of every Msh4 variant as compared with the genomic DNA sequence supports the high reliability of the methods of the present invention. The methods of the present invention enable isolation of polynucleotides that have unusual structures and are rarely contained in a cDNA library, such as β, δ, ε, θ, and τ. By utilizing the methods of the present invention, and based on the information obtained by genome project, a cDNA library that may called as "unusual cDNA library" may be constructed.

Thus, a simple method for accurate RACE is described herein. Its distinctive feature is the use of only a gene-specific primer, without an anchor or adaptor primer. The resultant products have a characteristic structure that contains a terminal inverted repeat made up of the gene-specific primer and occasionally nucleotides from its 3' flanking sequence. These structures suggest the following hypothetical mechanism of cDNA end synthesis (FIG. 3B). During cycle 1 (n), the targeted double-stranded cDNA is synthesized from a gene-specific primer. The linear DNA molecule tends to assume a circular format low concentration and at the temperature of 68° C. used for extension, the terminal region of the double-stranded DNA is partially denatured, as is observed at the cohesive end of the λ phage. Upon reaching the 5' end of the template DNA under these circumstances, Taq DNA polymerase may in some cases switch the template to the 5' terminal region of the newly synthesized daughter strand and then continue synthesizing DNA sequences complementary to the gene-specific primer, occasionally adding several nucleotides from the 3' flanking sequence (FIG. 3B). During cycle 2 (n+1), the targeted cDNA is amplified by PCR again using only the gene-specific primer. It is through this process that the resultant cDNA likely obtains its characteristic terminal inverted repeat.

The hypothetical mechanism summarized above explains the generation of a cDNA (MSH32) structure sandwiched between nested gene-specific primers (FIGS. 2A and C). In this case, during the first round of RACE PCR, sequences complementary to the gene-specific primer are added at the 3' end of the daughter strand synthesized from the 5' proximal gene-specific primer (#20) as a result of template switching. Then during the second round, the cDNA are amplified with the 5' proximal primer (#20) carried over from the first round sample (5 µl) as well as with the 3' proximal primer (#21) present at a higher (approx 10-fold) concentration in the reaction mixture. Template switching also appears to occur in the second round with MSH30 (FIG. 2A), leading to the formation of a terminal inverted repeat of primer #21 and its 3' flanking sequence, but the amount of DNA formed would be somewhat less than with MSH32 (Compare FIG. 1B-*a* and -*b* lane 4).

The terminal inverted repeat structure consisting of a gene-specific primer and several nucleotides from the 3' flanking sequence strongly suggests that synthesis of the cDNA end through DNA circularization and template switching (FIG. 3B) occur. Accordingly, it is possible that one may detect the circularized DNA molecule using electron microscopy. It is noteworthy that template switching has been observed during hepadnavirus reverse transcription, in which synthesis of the relaxed circular DNA genome of hepadnaviruses requires two template switches during plus-strand DNA synthesis: primer translocation, circularization. In that case, the ends of the minus-strand template are juxtaposed through base-pairing among three cis-acting sequences to facilitate the two template switches. The template switching with Taq DNA polymerase hypothesized here is not assumed to be exactly the same as with hepadnavirus reverse transcriptase since extensive base-pair interactions were not found among the 3' terminal sequences and the 3' flanking sequences of the switched site in the daughter strand (FIG. 4). This might mean that cDNA end synthesis by this mechanism is largely sequence-independent, enabling any mRNA to be identified by this method.

Primer dimers (homo- or heterodimers) have structures similar to the specific target cDNA synthesized using gene-specific primer(s) in the present study—i.e., they contain a terminal inverted repeat or are sandwiched between gene-specific primer(s) in a longer (1-2 kb) cDNA. Such dimeric primers are usually small in size (<100 bp), and the mechanism of their formation is believed to differ from that proposed here in that they are not derived from template DNA. Instead, it is the annealing of complementary sequences at the 3' end of the primer that causes amplification of homo- or heterodimeric primers, which makes it highly unlikely that specific synthesis of targeted cDNA containing a terminal inverted repeat or sandwiched between gene-specific primer(s) can be explained by primer dimer formation Furthermore, the terminal inverted repeat structure leading specific DNA synthesis might not be purely artifactual, as similar structures are contained within many viral and various transposable elements in organisms ranging from prokaryotes to mammals.

In summary, the single primer RACE method has been shown to be effective for identifying a rare splicing variant mRNA having an intriguing structure and function (Hirano and Noda, Gene, 2004, 342:165-177) and may also be applicable to comprehensive analysis of functional regions of genomic DNA using EST and/or SAGE databases as a primer source. The notable advantages of the single primer RACE method presented here are: (A) once double-stranded cDNAs are synthesized, they can be used as a cDNA library without adaptor ligation or cloning into a λ phage vector; (B) only a single gene-specific primer is necessary for screening a library using RACE PCR; (C) both 5' and 3' RACE can be done with the same cDNA library; (D) simple PCR protocols without complicated modifications are available for efficient RACE.

According to the present invention, methods for synthesizing polynucleotides having unknown nucleotide sequence in a region containing their 5'-end have been provided. When the methods of the present invention are applied to a cDNA second strand, 5' RACE can be carried out. The 5' RACE according to the present invention enables acquisition of cDNA longer at the 5'-side, which cannot be obtained by known methods. Furthermore, when the methods of the present invention are applied to a cDNA first strand, 3' RACE is also feasible. In the present invention, the same principle can be applied to both 5' RACE and 3' RACE.

According to the present methods for synthesizing polynucleotides, synthesis of polynucleotides having an unknown nucleotide sequence in a region containing their 5'-end is enabled by a simple procedure employing a reverse transcriptase, single primer, and a specific DNA polymerase. In other words, the present invention enables the synthesis of desired polynucleotides using an inexpensive and easy technique. Known methods, on the other hand, have been carried out based on complicated reactions wherein special primers are essential and a plurality of enzymes is required.

The methods of the present invention can efficiently synthesize desired polynucleotides. "Efficient" synthesis means that following features can be expected:
a region of unknown nucleotide sequence can be obtained in a longer state, and
unspecific reactions are suppressed.

As used herein, an unspecific reaction refers to the reaction of synthesizing a polynucleotide other than the desired polynucleotides. Specifically contemplated unspecific reactions include the formation of polynucleotides comprising a primer dimer, a structure in which plurality of cDNA fragments are linked, and such. By the above features, the 5' RACE and 3' RACE based on the present invention enable reliable acquisition of desired cDNA.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents and other references mentioned herein are incorporated by reference in their entirety. In case of conflict, the present specification, including definitions, will control. In addition, the materials, methods and examples are illustrative only and not intended to be limiting.

While the invention has been described in detail and with reference to specific embodiments thereof, it will be apparent to one skilled in the art that various changes and modifications can be made therein without departing from the spirit and scope of the invention.

SEQUENCE LISTING

<160> NUMBER OF SEQ ID NOS: 25

<210> SEQ ID NO 1
<211> LENGTH: 24
<212> TYPE: DNA
<213> ORGANISM: Artificial Sequence
<220> FEATURE:
<223> OTHER INFORMATION: Synthetic

<400> SEQUENCE: 1
ggtattgttg gcgacaggtt tctc                                           24

<210> SEQ ID NO 2
<211> LENGTH: 24
<212> TYPE: DNA
<213> ORGANISM: Artificial Sequence
<220> FEATURE:
<223> OTHER INFORMATION: Synthetic

<400> SEQUENCE: 2
gggatgccat ccttgtttga ttgc                                           24

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
aagagactgt caggcatggt agtg                                           24

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
gatgacttct ggatggggcc atgg                                      24

<210> SEQ ID NO 5
<211> LENGTH: 22
<212> TYPE: DNA
<213> ORGANISM: Artificial Sequence
<220> FEATURE:
<223> OTHER INFORMATION: Synthetic

<400> SEQUENCE: 5
gtgacgaggc ccagagcaag ag                                        22

<210> SEQ ID NO 6
<211> LENGTH: 27
<212> TYPE: DNA
<213> ORGANISM: Artificial Sequence
<220> FEATURE:
<223> OTHER INFORMATION: Synthetic

<400> SEQUENCE: 6
ccatcctaat acgactcact atagggc                                   27

<210> SEQ ID NO 7
<211> LENGTH: 42
<212> TYPE: DNA
<213> ORGANISM: Artificial Sequence
<220> FEATURE:
<223> OTHER INFORMATION: Synthetic

<400> SEQUENCE: 7
gggatgccat ccttgtttga ttgctaaagt ggatgcccca tg                  42

<210> SEQ ID NO 8
<211> LENGTH: 38
<212> TYPE: DNA
<213> ORGANISM: Artificial Sequence
<220> FEATURE:
<223> OTHER INFORMATION: Synthetic

<400> SEQUENCE: 8
ttactgacac tttagcaatc aaacaaggat ggcatccc                       38

<210> SEQ ID NO 9
<211> LENGTH: 43
<212> TYPE: DNA
<213> ORGANISM: Artificial Sequence
<220> FEATURE:
<223> OTHER INFORMATION: Synthetic

<400> SEQUENCE: 9
ggtattgttg gcgacaggtt tctcatttgg aaacaaaaga tct                 43

<210> SEQ ID NO 10
<211> LENGTH: 40
<212> TYPE: DNA
<213> ORGANISM: Artificial Sequence
<220> FEATURE:

<223> OTHER INFORMATION: Synthetic

<400> SEQUENCE: 10
aagagactgt caggcatggt agtgtatacg gccagtaagt                                    40

<210> SEQ ID NO 11
<211> LENGTH: 40
<212> TYPE: DNA
<213> ORGANISM: Artificial Sequence
<220> FEATURE:
<223> OTHER INFORMATION: Synthetic

<400> SEQUENCE: 11
tgggattaaa ggtatacact accatgcctg acagtctctt                                    40

<210> SEQ ID NO 12
<211> LENGTH: 42
<212> TYPE: DNA
<213> ORGANISM: Artificial Sequence
<220> FEATURE:
<223> OTHER INFORMATION: Synthetic

<400> SEQUENCE: 12
gatgacttct ggatggggcc atgtgagtcc aagacatgtg ag                                 42

<210> SEQ ID NO 13
<211> LENGTH: 40
<212> TYPE: DNA
<213> ORGANISM: Artificial Sequence
<220> FEATURE:
<223> OTHER INFORMATION: Synthetic

<400> SEQUENCE: 13
ttaggcttgc tcctcaccat ggccccatcc agaagtcatc                                    40

<210> SEQ ID NO 14
<211> LENGTH: 41
<212> TYPE: DNA
<213> ORGANISM: Artificial Sequence
<220> FEATURE:
<223> OTHER INFORMATION: Synthetic

<400> SEQUENCE: 14
gggatgccat ccttgtttga ttgctgtatt ggctagtttt g                                  41

<210> SEQ ID NO 15
<211> LENGTH: 42
<212> TYPE: DNA
<213> ORGANISM: Artificial Sequence
<220> FEATURE:
<223> OTHER INFORMATION: Synthetic

<400> SEQUENCE: 15
gagtttactg acactttagc aatcaaacaa ggatggcatc cc                                 42

<210> SEQ ID NO 16
<211> LENGTH: 28
<212> TYPE: DNA
<213> ORGANISM: Artificial Sequence
<220> FEATURE:
<223> OTHER INFORMATION: Synthetic

<400> SEQUENCE: 16
gaggccaggg tcctccgcat ggggcatc                                                 28

<210> SEQ ID NO 17
<211> LENGTH: 28
<212> TYPE: DNA
<213> ORGANISM: Artificial Sequence
<220> FEATURE:
<223> OTHER INFORMATION: Synthetic

<400> SEQUENCE: 17
ctgactacga agctggtctc aaatgact                28

<210> SEQ ID NO 18
<211> LENGTH: 28
<212> TYPE: DNA
<213> ORGANISM: Artificial Sequence
<220> FEATURE:
<223> OTHER INFORMATION: Synthetic

<400> SEQUENCE: 18
tatagcataa gatcttttgt ttccaaat                28

<210> SEQ ID NO 19
<211> LENGTH: 28
<212> TYPE: DNA
<213> ORGANISM: Artificial Sequence
<220> FEATURE:
<223> OTHER INFORMATION: Synthetic

<400> SEQUENCE: 19
cgtagggtaa gaactttttt atagacgt                28

<210> SEQ ID NO 20
<211> LENGTH: 28
<212> TYPE: DNA
<213> ORGANISM: Artificial Sequence
<220> FEATURE:
<223> OTHER INFORMATION: Synthetic

<400> SEQUENCE: 20
cctcacttgg cactcttact tactggcc                28

<210> SEQ ID NO 21
<211> LENGTH: 28
<212> TYPE: DNA
<213> ORGANISM: Artificial Sequence
<220> FEATURE:
<223> OTHER INFORMATION: Synthetic

<400> SEQUENCE: 21
gagacggagg actcacgacc ctaatttc                28

<210> SEQ ID NO 22
<211> LENGTH: 28
<212> TYPE: DNA
<213> ORGANISM: Artificial Sequence
<220> FEATURE:
<223> OTHER INFORMATION: Synthetic

<400> SEQUENCE: 22
tcattagcag ttgctcacat gtcttgga                28

<210> SEQ ID NO 23
<211> LENGTH: 28
<212> TYPE: DNA
<213> ORGANISM: Artificial Sequence
<220> FEATURE:
<223> OTHER INFORMATION: Synthetic

```
<400> SEQUENCE: 23
gtctgatcac cagtagaatc cgaacgag                                              28

<210> SEQ ID NO 24
<211> LENGTH: 28
<212> TYPE: DNA
<213> ORGANISM: Artificial Sequence
<220> FEATURE:
<223> OTHER INFORMATION: Synthetic

<400> SEQUENCE: 24
tcaagttgac acaaaactag ccaataca                                              28

<210> SEQ ID NO 25
<211> LENGTH: 28
<212> TYPE: DNA
<213> ORGANISM: Artificial Sequence
<220> FEATURE:
<223> OTHER INFORMATION: Synthetic

<400> SEQUENCE: 25
cgaagctggt ctcaaatgac tgtgaaat                                              28
```

What is claimed is:

1. A method for polynucleotide amplification comprising the steps of:
   (a) annealing a single gene specific primer to an interior region of a desired polynucleotide, wherein the desired polynucleotide has an unknown nucleotide sequence in a region comprising its 5'-end;
   (b) synthesizing a daughter strand complementary to the desired polynucleotide with a polymerase enzyme by using the desired polynucleotide as a template, wherein the desired polynucleotide and the daughter strand form a linear double stranded molecule;
   (c) incubating the linear double stranded molecule under conditions such that terminal but not interior regions of the double stranded molecule become denatured, wherein the polymerase enzyme undergoes strand switching;
   (d) synthesizing a nucleotide sequence complementary to the gene specific primer at the 3'-end of the daughter strand with the strand switched polymerase enzyme by using the 5' terminal region of the daughter strand as a template, wherein an elongated daughter strand is created; and
   (e) amplifying the desired polynucleotide with the polymerase enzyme by using the elongated daughter strand as a template and the single gene specific primer, wherein said amplifying is accomplished without the use of a further primer.

2. The method of claim 1, wherein the polynucleotide having the unknown nucleotide sequence in the 5'-end region is a cDNA second strand.

3. The method of claim 2, wherein the cDNA is synthesized using an mRNA in which a polynucleotide comprising a nucleotide sequence that is substantially the same as that of the gene specific primer of step (a) is added to the 5'-end, as a template.

4. The method of claim 2, comprising incubating the following (i) to (iii) under conditions where a complementary strand synthesis reaction is feasible:
   (i) a cDNA first strand;
   (ii) an enzyme catalyzing a template-dependent complementary strand synthesis reaction; and
   (iii) nucleotide substrates.

5. The method of claim 4, wherein the enzyme of (ii) that catalyzes the template-dependent complementary strand synthesis reaction has reverse transcriptase activity.

6. The method of claim 1, wherein the polynucleotide having the unknown nucleotide sequence in the 5'-end region is a cDNA first strand.

7. The method of claim 6, wherein the polynucleotide is a cDNA synthesized using an oligo-dT primer having an arbitrary nucleotide sequence added to its 5'-end.

8. A method for isolating a polynucleotide whose terminal nucleotide sequence is unknown, wherein the method comprises the step of cloning the polynucleotide synthesized by the method of claim 2.

9. A method for isolating a polynucleotide whose terminal nucleotide sequence is unknown, wherein the method comprises the step of cloning the polynucleotide synthesized by the method of claim 6.

10. The method of claim 1, wherein the desired polynucleotide is selected from the group consisting of DNA and RNA.

11. A method for screening mRNA samples, ds cDNA libraries, and genomic DNA libraries for a desired polynucleotide comprising the steps of:
   (a) amplifying the desired polynucleotide in accordance with the method steps of claim 1; and
   (b) screening mRNA samples, ds cDNA libraries, and genomic DNA libraries for the presence of the desired polynucleotide.

12. A method for identifying insertion sites of DNA elements at the nucleotide sequence level in the chromosomes of a mutant or transformed cell comprising the steps of:
   (a) extracting genomic DNA from a mutant or transformed cell;
   (b) digesting the genomic DNA;
   (c) amplifying the genomic ends of the extracted DNA using a single gene specific primer specific for a DNA element in accordance with the method steps of claim 1;

(d) screening for the presence of said DNA element; and
(e) identifying a site in which a DNA element has been inserted.

13. A method for identifying a site of chromosome or gene translocation at the nucleotide sequence level comprising the steps of:
   (a) isolating DNA or RNA from diseased cells known to result from chromosome or gene translocation;
   (b) amplifying the DNA or RNA in accordance with the method steps of claim 1; and
   (c) screening the amplified DNA or RNA for the presence of a chromosome or gene translocation using restriction mapping and polynucleotide sequencing techniques.

14. A method for polynucleotide amplification, comprising the steps of:
   (a) annealing a single gene specific primer to an interior region of a desired polynucleotide, wherein the desired polynucleotide comprises an unknown nucleotide sequence in a region comprising its 5'-end;
   (b) synthesizing a daughter strand complementary to the desired polynucleotide with polymerase enzyme by using the desired polynucleotide as a template, wherein the desired polynucleotide and the daughter strand form a linear double stranded molecule;
   (c) incubating the linear double stranded molecule under conditions such that terminal but not interior regions of the double stranded molecule become denatured, wherein the polymerase enzyme undergoes strand switching;
   (d) synthesizing a nucleotide sequence complementary to the gene specific primer at the 3'-end of the daughter strand with the strand switched polymerase enzyme by using the 5' terminal region of the daughter strand as a template, wherein said interior regions remain double stranded while an elongated daughter strand is created; and
   (e) amplifying the desired polynucleotide with the polymerase enzyme by using the elongated daughter strand as a template and the single gene specific primer, wherein said amplifying is accomplished without the use of a further primer.

* * * * *

UNITED STATES PATENT AND TRADEMARK OFFICE
CERTIFICATE OF CORRECTION

PATENT NO. : 7,504,240 B2
APPLICATION NO. : 11/078841
DATED : March 17, 2009
INVENTOR(S) : Masanori Hirano It is certified that error appears in the above-identified patent and that said Letters Patent is hereby corrected as shown below:

Column 5, line 2 should read : NO:9) and MSH32'3 (SEQ ID NO:8);

and

Columns 27-28 should read:

<210> SEQ ID NO 17
<211> LENGTH: 28
<212> TYPE: DNA
<213> ORGANISM: Artificial Sequence
<220> FEATURE:
<223> OTHER INFORMATION: Synthetic

<400> SEQUENCE: 17
tcagtaaact ctggtcgaag catcagtc                28

<210> SEQ ID NO 19
<211> LENGTH: 28
<212> TYPE: DNA
<213> ORGANISM: Artificial Sequence
<220> FEATURE:
<223> OTHER INFORMATION: Synthetic

<400> SEQUENCE: 19
tgcagatatt ttttcaagaa tgggatgc                28

Columns 27-29 should read:

<210> SEQ ID NO 21
<211> LENGTH: 28
<212> TYPE: DNA
<213> ORGANISM: Artificial Sequence
<220> FEATURE:
<223> OTHER INFORMATION: Synthetic

<400> SEQUENCE: 21

UNITED STATES PATENT AND TRADEMARK OFFICE
CERTIFICATE OF CORRECTION

PATENT NO. : 7,504,240 B2
APPLICATION NO. : 11/078841
DATED : March 17, 2009
INVENTOR(S) : Masanori Hirano It is certified that error appears in the above-identified patent and that said Letters Patent is hereby corrected as shown below:

ctttaatccc agcactcagg aggcagag    28

<210> SEQ ID NO 23
<211> LENGTH: 28
<212> TYPE: DNA
<213> ORGANISM: Artificial Sequence
<220> FEATURE:
<223> OTHER INFORMATION: Synthetic

<400> SEQUENCE: 23
gagcaagcct aagatgacca ctagtctg    28

Columns 29-30 should read:

<210> SEQ ID NO 25
<211> LENGTH: 28
<212> TYPE: DNA
<213> ORGANISM: Artificial Sequence
<220> FEATURE:
<223> OTHER INFORMATION: Synthetic

<400> SEQUENCE: 25
taaagtgtca gtaaactctg gtcgaagc    28

Signed and Sealed this

Thirteenth Day of October, 2009

David J. Kappos
*Director of the United States Patent and Trademark Office*